United States Patent
Sloat

(10) Patent No.: US 7,931,668 B2
(45) Date of Patent: Apr. 26, 2011

(54) MEDICAL TOOL WITH RETRACTIBLE HEADS

(76) Inventor: Glenn B. Sloat, Delmar, NY (US)

( * ) Notice: Subject to any disclaimer, the term of this patent is extended or adjusted under 35 U.S.C. 154(b) by 637 days.

(21) Appl. No.: 11/740,473

(22) Filed: Apr. 26, 2007

(65) Prior Publication Data

US 2008/0269799 A1 Oct. 30, 2008

(51) Int. Cl.
*A61B 17/00* (2006.01)

(52) U.S. Cl. ........................................................ 606/205

(58) Field of Classification Search .................. 606/205, 606/207; 81/427.5; 7/169
See application file for complete search history.

(56) References Cited

U.S. PATENT DOCUMENTS

| | | | |
|---|---|---|---|
| 420,125 A | 1/1890 | Swain | |
| 2,268,282 A | 12/1941 | Gary | |
| 2,608,953 A * | 9/1952 | Kollsman | 401/35 |
| 3,044,081 A | 7/1962 | Robinson, Jr. | |
| 3,484,924 A | 12/1969 | Dahl | |
| 3,818,784 A * | 6/1974 | McClure | 294/99.2 |
| 4,478,221 A * | 10/1984 | Heiss | 606/145 |
| 4,524,648 A | 6/1985 | Chung | |
| 5,782,853 A * | 7/1998 | Zeevi et al. | 606/187 |
| 6,182,541 B1 * | 2/2001 | Anderson et al. | 81/440 |
| 6,248,123 B1 | 6/2001 | McDonald | |
| 2002/0007705 A1 * | 1/2002 | Beauchamp | 81/490 |
| 2002/0174548 A1 | 11/2002 | Day | |

* cited by examiner

*Primary Examiner* — Eduardo C Robert
*Assistant Examiner* — Christopher Schubert
(74) *Attorney, Agent, or Firm* — Hoffman Warnick LLC

(57) ABSTRACT

A tool, such as a medical instrument that can provide a variety of different functions. Specifically, the present invention includes a variety of heads that each can allow the medical instrument to perform a different function. Each of the heads are operatively coupled to a holding apparatus of the medical instrument such as by the use of a sliding mechanism. In a preferred embodiment, the medical instrument is a forceps with heads operatively coupled to each arm. This coupling is done in such a way that a head can fully retract into a position such that no portion of the second medical head extends beyond the holding apparatus when not in use. This means that at most one of the heads extends from the holding apparatus of the medical instrument as any one time. As such, a doctor can use a single tool to perform multiple functions, and thus reduce time spent looking for and/or retrieving the appropriate tool.

11 Claims, 3 Drawing Sheets

MEDICAL TOOL WITH RETRACTIBLE HEADS

FIELD OF THE INVENTION

The present invention generally relates to medical equipment. Specifically, the present invention provides a versatile medical instrument, such as a forceps, that can be used in a variety of circumstances.

BACKGROUND OF THE INVENTION

In the medical profession, the amount of time that a task takes to perform can be critical. Having the correct medical instrument at a doctor's disposal can mean the difference between life and death. For this reason, doctors, especially in the surgical field, often equip large tables and/or trays with the wide array of medical instruments that they may need to perform a particular task.

However, in small hospitals and medical offices, limited space may make it impossible to keep the numerous medical instruments that are needed close at hand. In these situations, the doctor must prioritize the medical instruments that are nearby. As can be imagined, if a medical instrument that is not available is needed for the task, the doctor or an assistant must retrieve the medical instrument from storage and, if necessary, sterilize the medical instrument for use. As stated above, the time that must be expended in retrieving the correct instrument may be inconvenient at the least and disastrous at the worst.

In view of the foregoing, there exists a need for a solution that overcomes the shortcomings of the prior art.

SUMMARY OF THE INVENTION

In general, the present invention provides a medical instrument that can provide a variety of different functions. Specifically, the present invention includes a variety of heads that each can allow the medical instrument to perform a different function. Each of the heads is operatively coupled to a holding apparatus of the medical instrument such as by the use of a sliding mechanism. In a preferred embodiment, the medical instrument is a forceps with heads operatively coupled to each arm. This coupling is done in such a way that a head can fully retract into the holding apparatus when not in use. This means that at most one of the heads extends from the holding apparatus of the medical instrument at any one time. As such, a doctor can use a single tool to perform multiple functions, and thus reduce time spent looking for and/or retrieving the appropriate tool.

A first aspect of the present invention provides a medical instrument, comprising: an elongated holding apparatus having a first end and a second end; a first medical head operationally coupled to the holding apparatus so that the first medical head extends from the first end of the holding apparatus when in use and retracts into the first end of the holding apparatus when not in use; and a second medical head operationally coupled to the holding apparatus so that the second medical head extends from the first end of the holding apparatus when in use and retracts into the first end of the holding apparatus when not in use, wherein a maximum of one of the medical heads extends from the first end of a corresponding holding apparatus at any time.

A second aspect of the present invention provides a tool, comprising: first and second elongated holding apparatuses, each holding apparatus having a first end and a second end, the apparatuses being operationally coupled at the second ends; a first head slidably coupled to each of the holding apparatus so that each first head extends from the first end of the corresponding holding apparatus when in use and retracts into the first end of the holding apparatus when not in use; and a second head slidably coupled to each of the holding apparatus so that each first head extends from the first end of the corresponding holding apparatus when in use and retracts into the first end of the holding apparatus when not in use, wherein a maximum of one of the heads extends from the first end of a corresponding holding apparatus at any time.

Therefore, the present invention provides a versatile tool that may be used in the medical profession.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the present invention provides a medical instrument that can provide a variety of different functions. Specifically, the present invention includes a variety of heads that each can allow the medical instrument to perform a different function. Each of the heads is operatively coupled to a holding apparatus of the medical instrument such as by the use of a sliding mechanism. In a preferred embodiment, the medical instrument is a forceps with heads operatively coupled to each arm. This coupling is done in such a way that a head can fully retract into a position such that no portion of the second medical head extends beyond the holding apparatus when not in use. This means that at most one of the heads extends from the holding apparatus of the medical instrument as any one time. As such, a doctor can use a single tool to perform multiple functions, and thus reduce time spent looking for and/or retrieving the appropriate tool.

Figure 1:
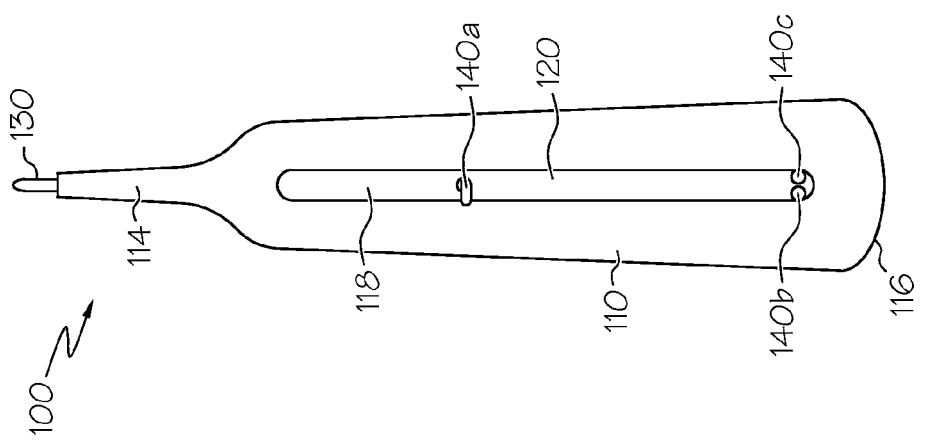
FIG. 1 shows a tool with a holding apparatus and a plurality of heads according to one embodiment of the claimed invention.

Referring now to FIG. 1, a tool 100 according to one embodiment of the present invention is shown. As stated herein, tool 100 is preferably a medical instrument. To this extent, tool 100 may be an instrument that is specifically designed for use in the medical field, for example, a forceps.

In any case, as indicated by FIG. 1, tool 100 includes an elongated holding apparatus 110 that has a first end 114 and a second end 116. In a preferred embodiment, holding apparatus 110 is designed in such a manner as to be of a size and shape for holding in the hand of a user. To this extent, holding apparatus 110 may be entirely or roughly flat, cylindrical, ovoid, rectangular, triangular, or like symmetrical shape or, in the alternative may be of irregular length, width and/or depth. Holding apparatus 110 may be entirely or roughly straight along its length or, in the alternative, may be curved in one or a variety of directions. In addition, holding apparatus 110 may be comprised of any material that is now known or later discovered to be useful for making tools, including, but not limited to metal, plastic, wood, stone, bone, polymer, ceramics and the like.

Extending from first end 114 of holding apparatus 110 is a first head 130. First head 130 will be described in further detail herein, but generally is operationally coupled to holding apparatus 110 in such a way that first head 130 extends from first end 114 of holding apparatus 110 when in use and retracts into a position relative to first end 114 of holding apparatus 110 such that no portion of first head 130 extends beyond first end 114 when first head 130 is not in use. Coupling of first medical 130 head and holding apparatus 110 is accomplished with the use of a coupler 140a-c. Coupler 140a-c will be described in further detail herein. In addition, holding apparatus 110 may include an access area 118, which allows a user to obtain access for extending and retracting first head 130.

Figure 2:
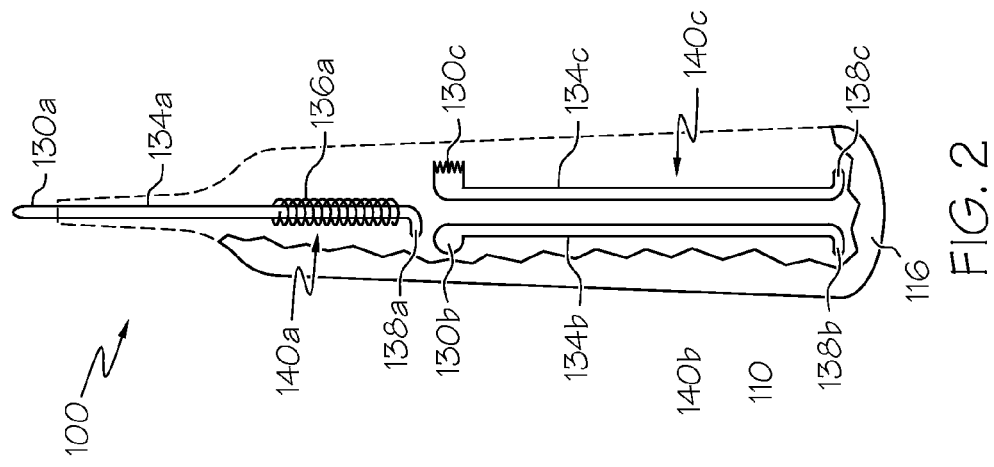
FIG. 2 shows a cutout view of a tool with a holding apparatus and a plurality of heads according to one embodiment of the claimed invention.
Figure 5:
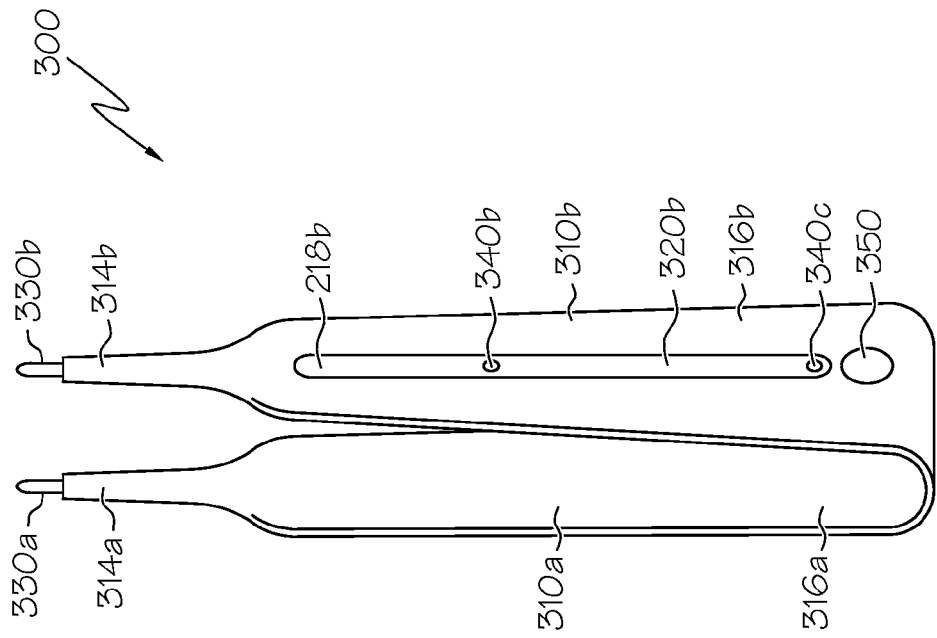
FIG. 5 shows a tool having two holding apparatuses according to one embodiment of the present invention.

In one embodiment, illustrated in FIGS. 1, 2 and 5, first head 130 completely retracts into first end 114 of holding apparatus 110 when not in use. In this embodiment, holding apparatus 110 includes a cavity into which first head 130 retracts when not in use. To this extent, first head 130 is fully or partially enclosed by holding apparatus 110 when not in use.

Figure 3:
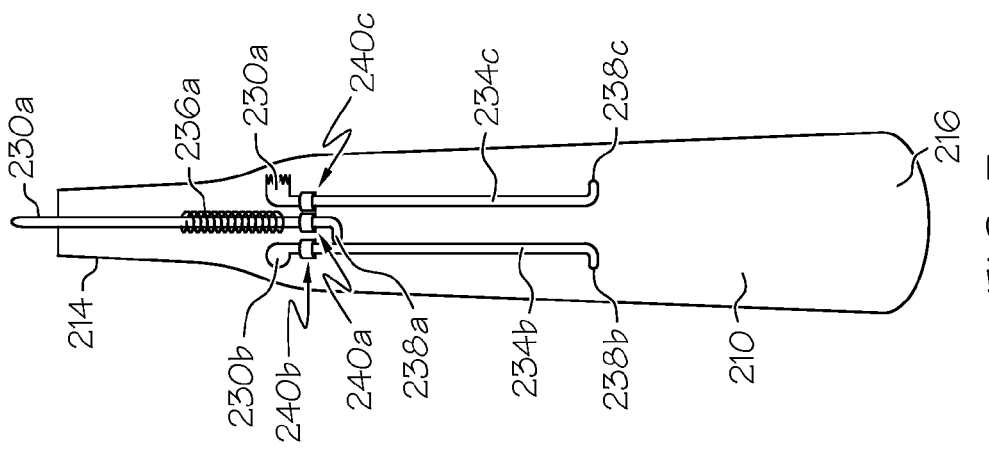
FIG. 3 shows a tool with a holding apparatus and a plurality of heads according to one embodiment of the claimed invention.

In contrast, in another embodiment, illustrated in FIG. 3, first head 230 retracts to a position alongside holding apparatus 210. When in the retracted position, no portion of first head 230 extends beyond first end 214 of holding apparatus 210. As such, each head may be retracted to a position such that no head extents beyond first end 214. In such a case, tool 200 may not be able to be utilized by a user in the case that first end 214 does not comprise a head in and of itself.

Referring now to FIG. 2 a cutout view of tool 100 according to one embodiment of the claimed invention is illustrated. As shown, tool 100 includes holding apparatus 110 with first end 114 and second end 116. Tool 100 also includes a first head 130a, a second head 130b, and a third head 130c. First head 130a, being in use, extends from first end 114 of tool 100. In contrast, second head 130b and third head 130c, not being in use, have been retracted into first end 114 of tool 100 and are enclosed within tool 100.

All three heads 130a-c are coupled to holding apparatus 110 with couplers 140a-c. As shown, couplers 140a-c each include a coupler access 138a-c and a coupler connector 134a-b. Coupler access 138a-c is generally found within access area 118 (FIG. 1) of holding apparatus 110. Coupler connector 134a-c connects coupler access 138a-c and heads 130a-c to allow a user to extend and retract each head 130a-c in turn by activating each coupler access 138a-c.

In the illustrated embodiment, coupler 140a-c slidably couples heads 130a-c and holding apparatus 110. In this embodiment, access area 118 (FIG. 1) comprises a channel through which coupler access 138a-c can slide. A user who wishes to extend one of heads 130a-c, such as second head 130b, would move coupler access 138a along access area 118 (FIG. 1) channel, causing head 130b to extend from first end 114 of holding apparatus 110. As a maximum of one of heads 130a-c may extend from first end 114 of holding apparatus 110 at any time, if one of heads 130a-c, such as first head 130a was already extending from first end 114 of holding apparatus 110, first head 130a would have to be retracted before second head 130b could be extended. This retraction of first head 130a may require a user to manually activate coupler access 138a, or, in the alternative, may be accomplished automatically using a retractor mechanism 136a. Although, retractor mechanism 136a is illustrated as a spring any solution for retracting that is now known or later developed may be used.

In an alternative embodiment, coupler 140a-c may include a rotary device (not illustrated) for extending and retracting heads 130a-c. In this embodiment, access area 118 (FIG. 1) would include an aperture in which rotary device is contained. Coupler could include a threaded portion, such as a portion of coupler connector 134a-c. A user that desires to extend a particular one of heads 130a-c would rotate the rotary device, causing the desired one of heads 130a-c to extend or retract as needed.

In yet another embodiment, extending and retracting of heads 130a-c could be accomplished automatically such as by way of an electric motor. In this embodiment, coupler access 138a-c could include a switch, button, or the like mounted in coupler access area 118 (FIG. 1). In yet still another embodiment, multiple heads 138a-c may be coupled to holding apparatus 110 using a single coupler 140. In yet still another embodiment one or more locking mechanisms (not shown) may be included for temporarily locking heads 138a-c in an extended 138a position, a retracted 138b-c position or any other position that may be desired. In short, any way now known or later developed for extending and/or retracting an item may be used.

Referring now to FIG. 3 a cutout view of tool 200 according to an alternative embodiment of the claimed invention is illustrated. As shown, tool 200 includes holding apparatus 210 with first end 214 and second end 216. Tool 200 also includes a first head 230a, a second head 230b, and a third head 230c. First head 230a, being in use, extends beyond first end 214 of tool 200. In contrast, second head 230b and third head 230c, not being in use, have been retracted into a position such that they do not extend beyond first end 214 of tool 200.

All three heads 230a-c are coupled to holding apparatus 210 with couplers 240a-c. As illustrated, all three heads 230a-c are coupled to the same surface of holding apparatus; however, it should be appreciated that one or more of heads 230a-c may be coupled to one surface while one or more are coupled to a different surface. As shown, couplers 240a-c each include a coupler access 238a-c and a coupler connector 234a-b, which is in some way coupled to holding apparatus 210. Coupler connector 234a-c connects coupler access 238a-c and heads 230a-c to allow a user to extend and retract each head 230a-c in turn by activating each coupler access 238a-c.

In the illustrated embodiment, coupler 240a-c slidably couples heads 230a-c and holding apparatus 210. A user who wishes to extend one of heads 230a-c, such as second head 230b, would move coupler access 238a causing head 230b to extend from first end 214 of holding apparatus 210. As a maximum of one of heads 230a-c may extend from first end 214 of holding apparatus 210 at any time, if one of heads 230a-c, such as first head 230a was already extending from first end 214 of holding apparatus 210, first head 230a would have to be retracted before second head 230b could be extended. This retraction of first head 230a may require a user to manually activate coupler access 238a, or, in the alternative, may be accomplished automatically using a retractor mechanism 236a. Although, retractor mechanism 236a is illustrated as a spring any solution for retracting that is now known or later developed may be used.

In an alternative embodiment, coupler 240a-c may include a rotary device (not illustrated) for extending and retracting heads 230a-c. In this embodiment, a rotary device coupler would couple the rotary device to holding apparatus 210. Coupler could include a threaded portion, such as a portion of coupler connector 234a-c. A user that desires to extend a particular one of heads 230a-c would rotate the rotary device, causing the desired one of heads 230-c to extend or retract as needed.

In yet another embodiment, extending and retracting of heads 230a-c could be accomplished automatically such as by way of an electric motor. In this embodiment, coupler access 238a-c could include a switch, button, or the like coupled to holding apparatus. In yet still another embodiment, multiple heads 238a-c may be coupled to holding apparatus 210 using a single coupler 240. In yet still another embodiment one or more locking mechanisms (not shown) may be included for temporarily locking heads 238a-c in an extended 238a position, a retracted 238b-c position or any other position that may be desired. In short, any way now known or later developed for extending and/or retracting an item may be used.

Figure 4:
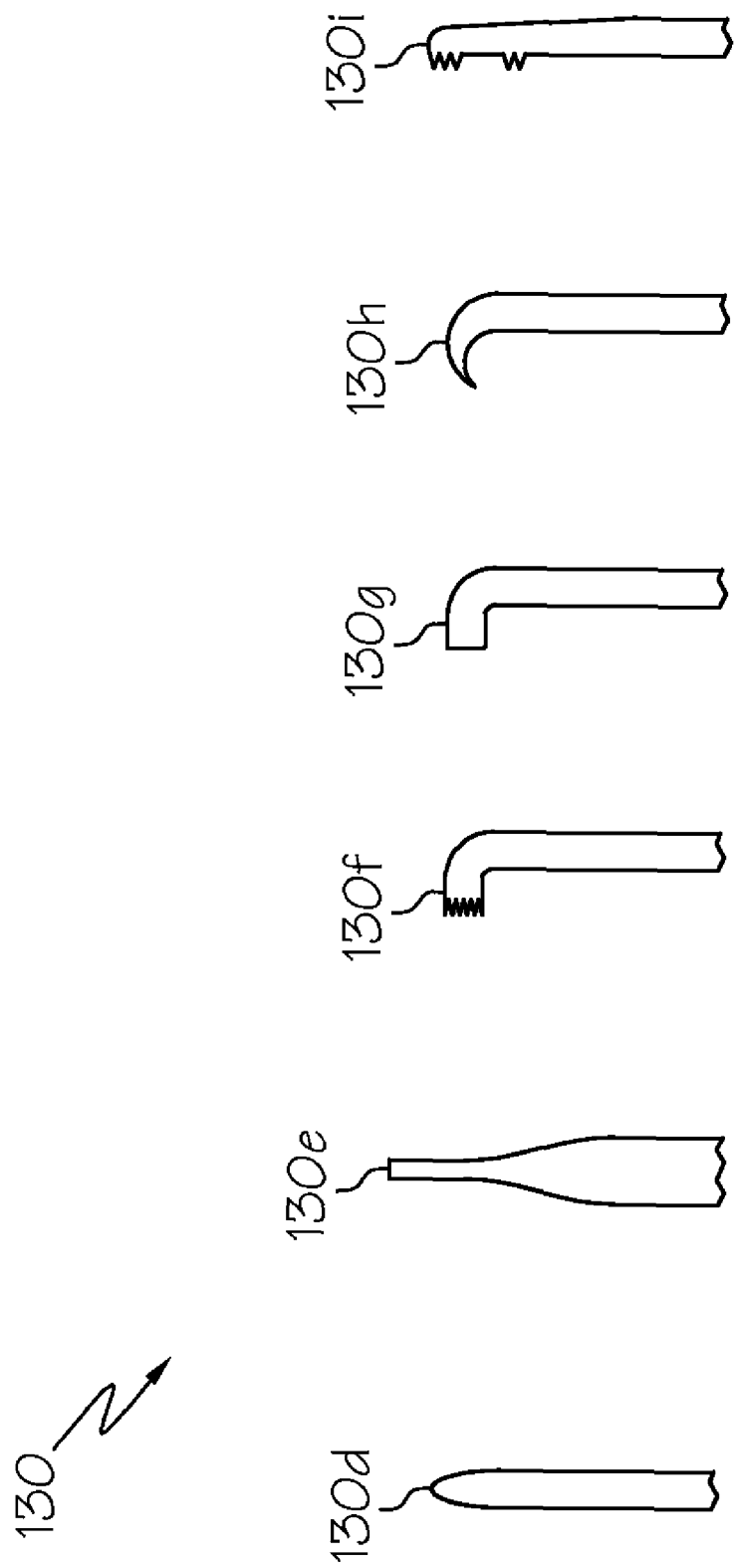
FIG. 4 shows a variety of heads for a tool according to one embodiment of the claimed invention.

Referring now to FIG. 4 a variety of configurations for heads 130d-i are shown, which may correspond to heads 130a-c, heads 230a-c and/or heads 330a-c. As shown, heads 130d-i may include a fine tip head 130d, a very fine tip head 130e, an extended tip with teeth 130f, an extended tip without teeth, an extended tip with a point 130h, or a tip with teeth along all or a portion of the head 130i. In the alternative, head 130a-i may take on any configuration now known or later discovered to be useful in the art. In addition, head 130a-i may be comprised of any material that is now known or later discovered to be useful for making tools, including, but not limited to metal, plastic, wood, stone, bone, polymer, ceramics and the like.

Referring now to FIG. 5 a tool 300 according to a preferred embodiment of the present invention is illustrated. As shown in FIG. 4, tool 300 includes a first holding apparatus 310a and a second holding apparatus 310b. The holding apparatuses 310a-b may be elongated and may be of roughly the same shape and/or size or may differ in shape and or size as needed by the user. Holding apparatuses 310a-b are coupled at or about the second ends 316a-b using a holding apparatus coupler 350. Holding apparatus coupler 350 may include a rivet, screw, leaf spring, weld or the like. When holding apparatuses 310a-b are coupled together to form tool 300, tool 300 may comprise a tool for holding and/or clamping, such as a forceps.

Each of the holding apparatuses 310a-b may have a plurality of heads 330a-b. As shown, heads 330a-b are coupled to the apparatuses in similar fashion to those described herein with reference to tool 100 (FIGS. 1 and 2), however a coupling in similar fashion to those described in FIG. 3 is also envisioned. Each of the holding apparatuses 214a-b may have heads 230a-b of identical type or, in the alternative, one or more heads 230a in holding apparatus 214a may be different from one or more heads 230b in holding apparatus 214b. In addition, holding apparatuses 214a-b may contain an identical number of heads 230a-b or, in the alternative, holding apparatus 214a may contain more or fewer heads 230a than holding apparatus 214b.

While shown and described herein as a tool, it is understood that the invention further provides various alternative embodiments. For example, while various figures illustrate embodiments that include one, two or three heads, it should be appreciated that any number of heads that are desired may be incorporated. To this extent, the foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

I claim:

1. A medical instrument, comprising:
    a single elongated holding apparatus having a first end and a second end the holding apparatus being adapted to be held by a user when used by the user;
    a second elongated holding apparatus having a first end and a second end, the second end of the second holding apparatus being operationally coupled to the second end of the holding apparatus;
    a first medical head operationally coupled to the holding apparatus so that the first medical head extends from the first end of the holding apparatus when in use and retracts into a position such that no portion of the second medical head extends beyond the first end of the holding apparatus when not in use;
    a fourth medical head corresponding to the first medical head and being operationally coupled to the second holding apparatus so that the forth medical head extends from the first end of the second holding apparatus when in use and retracts into a position such that no portion of the second medical head extends beyond the first end of the holding apparatus when not in use, wherein the fourth medical head is adapted to be used in conjunction with the first medical head;
    a second medical head operationally coupled to the holding apparatus so that the second medical head extends from the first end of the holding apparatus when in use and retracts into a position such that no portion of the second medical head extends beyond the first end of the holding apparatus when not in use; and
    a fifth medical head corresponding to the first medical head and being operationally coupled to the second holding apparatus so that the fifth medical head extends from the first end of the second holding apparatus when in use and retracts into a position such that no portion of the fifth medical head extends beyond the first end of the second holding apparatus when not in use, wherein the fifth medical head is adapted to be used in conjunction with the second medical head,
    wherein a maximum of one of the medical heads extends from the first end of a corresponding holding apparatus at any time, and
    wherein the first and fourth medical heads operate together as a clamp and wherein the second and fifth medical heads operate together as an alternately configured clamp, and wherein the first and second medical heads are slidably coupled to the holding apparatus.

2. The instrument of claim 1, further comprising a third medical head operationally coupled to the holding apparatus so that the third medical head extends from the first end of the holding apparatus when in use and retracts into the first end of the holding apparatus when not in use.

3. The instrument of claim 2, wherein the first medical head, the second medical head, and the third medical head retract into the first end of the holding apparatus when not in use and wherein the fourth medical head and the fifth medical head retract into the first end of the second holding apparatus when not in use.

4. The instrument of claim 1, wherein the first medical head retracts into the first end of the holding apparatus when not in use, and wherein the second medical head retracts into the first end of the holding apparatus when not in use.

5. The instrument of claim 1, wherein the medical instrument is a forceps.

6. A tool, comprising:
   first and second elongated holding apparatuses, each holding apparatus having a first end and a second end, the apparatuses being operationally coupled at the second ends the first and second holding apparatuses being adapted to be held by a user when used by the user;
   a pair corresponding first heads, one first head being slidably coupled to each of the holding apparatus so that each first head extends from the first end of the corresponding holding apparatus when in use and retracts into a position such that no portion of the second medical head extends beyond the first end of the holding apparatus when not in use, wherein the first heads operate together as a clamp; and
   a pair corresponding second heads different from the first heads, one second head being slidably coupled to each of the holding apparatus so that each second head extends from the first end of the corresponding holding apparatus when in use and retracts into a position such that no portion of the second medical head extends beyond the first end of the holding apparatus when not in use, second heads operate together as an alternately configured clamp,
   wherein a maximum of one of the heads extends from the first end of a corresponding holding apparatus at any time.

7. The tool of claim 6, wherein the tool is a medical instrument.

8. The tool of claim 7, wherein the medical instrument is a forceps.

9. The tool of claim 6, wherein the first head and the second head retract into the first end of the holding apparatus when not in use.

10. The tool of claim 6, further comprising a third head slidably coupled to each of the holding apparatus so that each first head extends from the first end of the corresponding holding apparatus when in use and retracts into a position such that no portion of the second medical head extends beyond the first end of the holding apparatus when not in use.

11. The tool of claim 10, wherein each of the first heads retracts into the first end of the corresponding holding apparatus when not in use, and wherein each of the second heads retracts into the first end of the corresponding holding apparatus when not in use, and wherein the third head retracts into the first end of the holding apparatus when not in use.

* * * * *